US00PP07810P

United States Patent [19]

Drewlow

[11] Patent Number: Plant 7,810

[45] Date of Patent: Feb. 25, 1992

[54] KALANCHOE PLANT NAMED HEIRLOOM

[75] Inventor: Lyndon W. Drewlow, Ashtabula, Ohio

[73] Assignee: Mikkelsens, Inc., Ashtabula, Ohio

[21] Appl. No.: 607,441

[22] Filed: Oct. 31, 1990

[51] Int. Cl.[5] ..... A01H 5/00
[52] U.S. Cl. ..... Plt./68
[58] Field of Search ..... Plt./68

*Primary Examiner*—James R. Feyrer
*Attorney, Agent, or Firm*—Foley & Lardner

[57] ABSTRACT

A new and distinct cultivar of Kalanchoe plant named Heirloom, characterized by its oblong shaped lavender pink flowers, early flowering, non-splitting flowers, dark green, curled leaves, good flower keeping qualities, mounded growth habit, and its dense inflorescence.

1 Drawing Sheet

The present invention relates to a new and distinctive cultivar of Kalanchoe plant, botanically known as Kalanchoe, and known by the cultivar name Heirloom. Heirloom was discovered by me as a spontaneous color mutation of Bingo, a cultivar disclosed in U.S. Plant Pat. No. 5,876. Heirloom was discovered while growing among a block of flowering plants of the parent cultivar in greenhouses in Ashtabula, Ohio. The new cultivar was noted due to its lighter, lavender pink flower, and subsequent development of Heirloom led to the discovery of other distinguishing characteristics, which will be noted below.

Asexual reproduction of Heirloom by stem cuttings has shown that the unique features of this new Kalanchoe are stabilized and are reproduced true to type in successive propagations.

The following characteristics distinguish the new kalanchoe from both its parent variety and other cultivated kalanchoe of this type known and used in the floriculture industry, including comparison cultivar Dignity, disclosed in U.S. Plant Pat. No. 5,255. Color references are to the Royal Horticultural Society Colour Chart (R.H.S.).

1. Heirloom has lavender pink flowers (62A to 63C) while Bingo has deeper lavender pink flowers (67C to 68A) and Dignity has lighter pink to salmon flowers which, depending on age, range in color from 37A to 55B and C.

2. Flowering time for Heirloom and Bingo are 4 to 7 days earlier than Dignity under summer conditions, and they are both 14 or more days earlier than Dignity under winter conditions.

3. Heirloom's flower petals are much more oblong in shape than either Bingo or Dignity, both of which have a much more rounded petal.

4. Heirloom flowers do not split (calyx opens allowing flower petals to separate), while Bingo can experience severe splitting under certain environmental conditions, and Dignity small amounts of splitting.

5. Heirloom and Bingo have similar shaped leaves with a curled appearance, while Dignity has leaves that are flatter and more oblong in shape. All three are similar in green color.

6. Average height of Heirloom and Bingo is 20 to 22 cm, while Dignity is 23 to 25 cm in height when grown under similar conditions.

7. Heirloom and Bingo have individual flowers that last four days or longer than the flowers of Dignity. The length of time plants remain in bloom after start of short day treatment is up to two weeks longer for Heirloom and Bingo when compared to Dignity.

8. Heirloom and Bingo have a more mounded appearance because lateral branches don't grow as long as the terminal shoot, whereas Dignity is more upright in habit because laterals grow to the same length as terminal shoot.

9. Bingo and Heirloom have a more dense inflorescence covered solid with flowers, while Dignity has fewer flowers in the inflorescence on a more open growth habit.

The accompanying colored photograph illustrates in front perspective view the overall appearance of Heirloom, showing the colors as true as it is reasonably possible to obtain in a colored reproduction of this type. The photograph was taken on Mar. 23, 1990 under natural light on an overcast day, and under double poly greenhouse covering at Ashtabula, Ohio.

The following is a detailed description of my new cultivar, based on plants produced in greenhouses in Ashtabula, Ohio during the late spring to summer season of the year. Plants were grown in 10 cm pots and measurements were taken 12 weeks after rooted cuttings were planted. Height measurements were taken from the soil line of the container. The plants were grown at 65°-68° F. night temperatures, under 3500-4000 foot candles of light, and 240 ppm nitrogen, 240 ppm potassium, and 175 ppm phosphorous nutritional levels with trace elements added. 5000 ppm B-9 was applied week three and week five of short day treatment of the six week short day treatment (14 hours dark) period. Habit of growth, plant height, flowering time, size of leaves and peduncle length will be greatly influenced by nutritional and environmental conditions.

Colors references are made to the Royal Horticultural Society Colour Chart except where general terms of ordinary dictionary significance are used.

Parentage: Spontaneous mutation from the cultivar Bingo.

Propagation:

(A) *Type cutting.*—Stem tip cutting up to 3 cm long.

(B) *Time to root.*—10 days at 21° C. in summer; 14 days at 21° C. in winter.

(C) *Rooting habit.*—Abundant, fine, fibrous roots.

Plant description:

(A) *Habit and form of growth.*—Compact; flower clusters are held well above foliage; good basal branching; semi-upright; environment and use of growth regulators will play a role in final height and shape.

(B) *Foliage description.*—Leaves simple and opposite. 1. Size: Average; full grown leaves on a plant when grown in a 10 cm pot are 10.5 to 11.5 cm long and 7.5 to 8.0 cm wide. 2. Shape: Ovate; apex obtuse; base acute. 3. Texture: Glabrous, coriaceous, and succulent. 4. Margin: Crenate; shallow lobed. 5. Color: Young foliage, top side 146A; under side 146B; mature foliage, top side 147A; under side 147B.

Flowering description:

(A) *Flowering habits.*—Inflorescence is a cyme. Terminal flower on main axis opens first, followed by the terminal flowers of the side branches from the upper nodes, continuing with the subsequent development of branches in the inflorescence. Inflorescence is made up of the main stem and six or more lateral branches.

(B) *Natural flowering season.*—Early January. Flowering time under controlled day length at 20° C. in summer is 10 weeks; in winter 11½ weeks. Flowering time depends on temperature, light intensity and other growing conditions.

(C) *Flower buds.*—Oblong, up to 6 mm long before showing color, developing tubular as flower petals mature; sheathed in four green sepals.

(D) *Flowers borne.*—Compound dichasial cymes; primary peduncle 4 mm in diameter just below the first branch of the inflorescence; length will vary depending on growing conditions. Pedicels vary in length depending on where they are located in the inflorescence.

(E) *Quantity of flowers.*—Very floriferous as main stem has 50 or more flowers and each of the six or more lateral branches have 30 to 50 flowers.

(F) *Petals.*—1. Shape: Oblong; top cuspidate. 2. Color, top side when opening: 62A to 63C, fading to 62B to 63D; under side 62B. 3. Number of petals; Four. 4. Size: Individual petals 6 mm wide and 7.5 mm long; flowers 16 mm in diameter.

(G) *Reproductive organs.*—1. Stamens: Number, 8. a. Anther shape: Flat, elliptical, color yellowish green. b. Filament color: Whitish green. c. Pollen color: Yellow. 2. Pistils: a. Stigma shape: Flat; color immature, yellow green; mature white. b. Style color: Light green. c. Ovaries: Four; size 5 mm; color green.

Disease resistance: Heirloom has shown resistance to powdery mildew, and no other disease problems have been noted to date.

Other important characteristics: Heirloom is part of a series of Kalanchoe plants that include Majestic, Splendor, Keepsake, and Revelry (all are disclosed in pending plant patent applications of applicant) that are similar in flowering time, height, branching and response to growth regulators. This allows the greenhouse growers to handle all five distinctively different colors at the same time from a single planting date and use the same growing methods on each to end up with a uniform crop. The end results are easier crops for the growers to produce and higher quality crops. All of these cultivars are ideal for 10 and 15 cm pot production.

I claim:

1. A new and distinct cultivar of Kalanchoe plant named Heirloom, as illustrated and described.

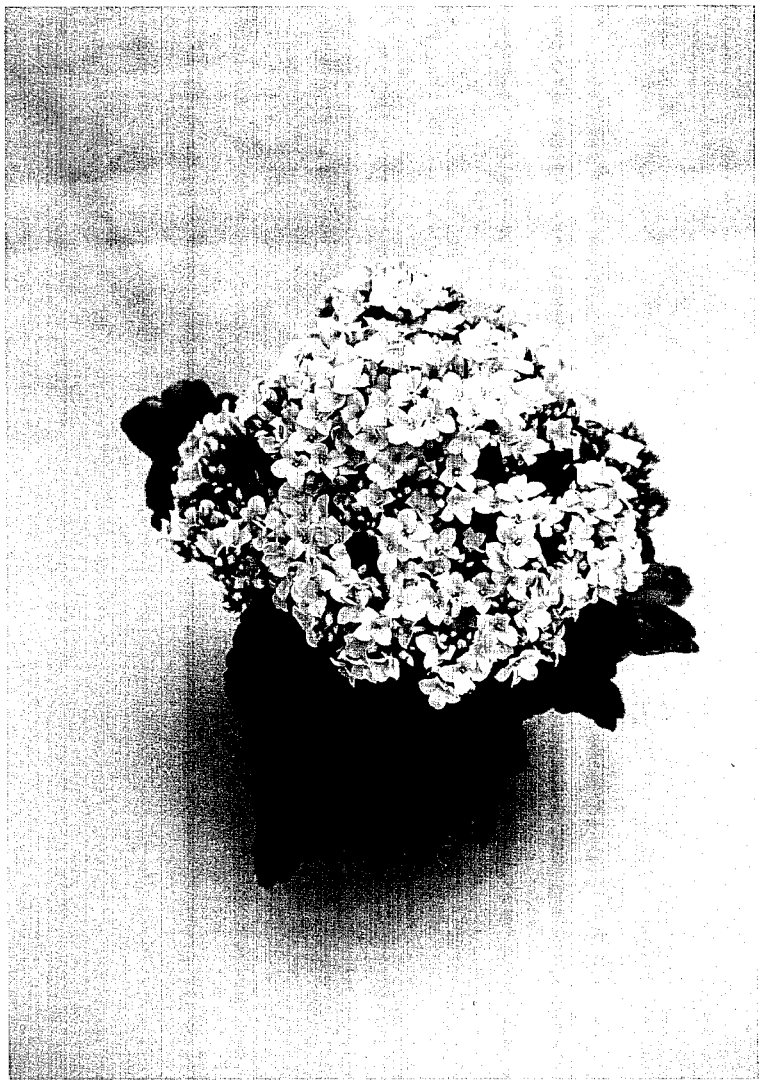

* * * * *